United States Patent [19]

Firth et al.

[11] Patent Number: 4,465,871

[45] Date of Patent: Aug. 14, 1984

[54] PREPARATION OF 2-T-BUTYL-4-ALKOXY- AND 4-HYDROXYPHENOLS

[75] Inventors: Bruce E. Firth, Arlington Heights, Ill.; Terry J. Rosen, Berkeley, Calif.

[73] Assignee: UOP Inc., Des Plaines, Ill.

[21] Appl. No.: 521,479

[22] Filed: Aug. 8, 1983

Related U.S. Application Data

[63] Continuation-in-part of Ser. No. 440,676, Nov. 10, 1982, Pat. No. 4,447,657.

[51] Int. Cl.³ .................... C07C 39/04; C07C 37/00
[52] U.S. Cl. ................................................ 568/783
[58] Field of Search .................. 568/783, 805, 806

[56] References Cited

U.S. PATENT DOCUMENTS

| | | | |
|---|---|---|---|
| 1,835,344 | 12/1931 | Schoeller et al. | 568/783 |
| 2,289,886 | 7/1942 | Schmerling | 568/783 |
| 4,283,572 | 8/1981 | Klicker | 568/783 |
| 4,381,413 | 4/1983 | Dodd | 568/806 |

FOREIGN PATENT DOCUMENTS

| | | | |
|---|---|---|---|
| 2345911 | 3/1975 | Fed. Rep. of Germany | 568/783 |
| 432123 | 11/1974 | U.S.S.R. | 568/783 |

OTHER PUBLICATIONS

Dewar et al., "Jour. Chem. Soc.", (1959), pp. 4080–4086, 4089–4095.
Dewar et al., "Jour. Chem. Soc.", (1960), pp. 959–963.

*Primary Examiner*—Werren B. Lone
*Attorney, Agent, or Firm*—James R. Hoatson, Jr.; Eugene I. Snyder; William H. Page, II

[57] ABSTRACT

Tertiary alkyl phenyl ethers may be induced to undergo thermal rearrangement on an alumina catalyst to afford the isomeric ortho-t-alkylphenol. Such rearrangement generally occurs under milder conditions than does the alkylation of a phenol with an olefin using the same alumina as an alkylating catalyst. The rearrangement remains regioselective even when the phenyl ring bears an alkoxy group, hence affords a good preparative route to such materials as 2-t-butyl-4-methoxyphenol.

17 Claims, No Drawings

PREPARATION OF 2-T-BUTYL-4-ALKOXY- AND 4-HYDROXYPHENOLS

CROSS-REFERENCE TO RELATED APPLICATION

This application is a continuation-in-part of our copending application, Ser. No. 440,676, filed Nov. 10, 1982, which is incorporated by reference.

BACKGROUND OF THE INVENTION

Alkylphenols are materials of commerce desirable for their antioxidant properties. Many members of this class have commercial utility in such applications as antioxidants and stabilizing agents for fuel oils and antioxidants for foods of diverse type. Among the phenols which are antioxidants the ortho-alkyl- and ortho, ortho-dialkylphenols appear to be superior. That is to say, the ortho-alkylphenols and ortho, ortho-dialkylphenols seem to be better antioxidants than their isomers. There is a corresponding need to prepare such ortho-alkylated phenols with relatively high selectivity and yield.

The usual method of preparing alkylphenols is to alkylate phenols with an olefin, alkyl halide, or alcohol in the presence of an alkylating catalyst which generally is a Lewis acid. Catalysts which have been employed include strong inorganic acids (sulfuric acid, phosphoric acid, and hydrofluoric acid to name a few), strong organic acids (for example, sulfonic acids and cationic exchange resins bearing such acid functionalities), metal halides (boron trifluoride, aluminum halides, and zinc halides are exemplary) and inorganic oxides such as alumina and silica. A deficiency in all such methods is their limited selectivity for alkylation at available positions ortho to the hydroxyl group vis-a-vis alkylation at other available positions. This limitation is particularly acute where the phenol bears another substituent, e.g., an alkoxy moiety, which is comparable to the hydroxyl group in effecting ortho-alkylation. Since 2-t-butyl-4-alkoxyphenols are generically especially desirable antioxidants, as exemplified by the broad usage of 2-t-butyl-4-methoxyphenol, popularly known as BHA, the lack of selectivity discussed above has great economic impact.

Some instances of the rearrangement of alkyl phenyl ethers to the isomeric alkylphenol have been reported. For example, U.S. Pat. No. 2,289,886 discloses that alkyl phenyl ethers when treated with hydrogen fluoride afford both the isomeric alkylphenol and the dealkylated phenol. More recently U.S. Pat. No. 4,283,572 describes the rearrangement of nonyl phenyl ether to a mixture of phenol, mononoylphenol, and dinonylphenol. Such sparse reports are in marked contrast to the well-known thermal rearrangement of allyl phenyl ethers to allyl phenols (Claisen arrangement) where the allyl group migrates selectively to an ortho or, less often, to a para position.

We have made the remarkable discovery that alkyl phenyl ethers undergo a thermal rearrangement in the presence of an alumina as catalyst to afford the isomeric ortho-alkylphenols with high yield and good selectivity. Not only is the thermal rearrangement of an alkyl phenyl ether to an alkylphenol without precedent as a general phenomenon, at least at the temperatures used herein, but the regioselectivity of the rearrangement to afford an ortho-alkylphenol is completely surprising. That this regioselectivity persists when the alkyl group is a t-butyl moiety and when the aromatic ring bears another alkoxy group para to the t-butyl ether moiety is totally unexpected, and is the basis of our process of making 2-t-butyl-4-alkoxyphenols.

Such a method of making an ortho-alkylphenol has many advantages over the prior art methods in addition to the observed regioselectivity. One advantage is formation of the ortho-alkylphenol at a substantially lower temperature than was previously possible. That is to say, the rearrangement occurs at a temperature lower than that necessary for alkylation of the phenol with, for example, an olefin using an alumina as the alkylating catalyst. Since the alkyl phenyl ether may be prepared from a phenol under relatively mild conditions, our discovery makes possible a two-stage preparation of an alkylphenol via 1) formation of alkyl phenyl ether followed by 2) rearrangement of the ether, both reactions proceeding under substantially milder conditions than direct alkylation of the phenol.

Another important advantage of our method is the strict control it affords over the degree of alkylation. Thus, since only the alkyl group of an alkyl phenyl ether migrates to the ortho position our process is tantamount to exclusive monoalkylation. Because monoalkylation of phenols, e.g., 4-methylphenol, often is plagued by overalkylation to give undesired products, e.g., 2,6-di-t-butyl-4-methylphenol, our method is unique in affording exclusive monoalkylation.

Still another advantage of the method which is our invention is that it affords products which sometimes are not otherwise readily available. For example, ethers of an (2-alkylphenyl) alkyl ether undergo rearrangement to the isomeric 2,6-dialkylphenol with great specificity, whereas direct alkylation of the same 2-alkylphenol may fail to afford the desired 2,6-dialkylphenol, or do so only in relatively poor yield.

SUMMARY OF THE INVENTION

An object of the invention described herein is to prepare ortho-alkylphenols by rearrangement of the isomeric alkyl phenyl ethers. One embodiment is a method of rearrangement which is thermally induced on an alumina catalyst. In a more specific embodiment the catalyst is a fluorided alumina and the temperature is from about 75° to about 200° C.

Another object of our invention is to alkylate phenols selectively at the ortho position by converting the phenol to an alkyl phenyl ether and rearranging the latter in a thermal reaction on an alumina catalyst. In a specific embodiment the reactant phenol is a 4-alkoxyphenol, the ether is a t-alkyl 4-alkoxyphenyl ether, and the product is a 2-t-alkyl-4-alkoxyphenol.

DESCRIPTION OF THE INVENTION

In one aspect, the invention described herein is a method of rearranging a t-alkyl 4-alkoxyphenyl ether or a t-alkyl 4-hydroxyphenyl ether to its isomeric ortho-t-alkylphenol comprising heating said ether in contact with an alumina under rearrangement conditions and recovering the ortho-t-alkylphenol. In another aspect our invention is a method of ortho-alkylating a 4-alkoxy- or 4-hydroxyphenol comprising converting the phenol to a t-alkyl phenyl ether, thermally rearranging the ether in the presence of an alumina catalyst, and recovering the formed ortho-t-alkylphenol.

We have found that alkyl phenyl ethers can be induced to undergo thermal rearrangement in contact with an alumina. The alkyl group may be an unsubstituted alkyl, i.e., $C_nH_{2n+1}$, or it may be a substituted alkyl group where the substituent is otherwise inert under the reaction conditions. Examples of inert substituents include the halogens, a substituted or unsubstituted amino group, an aryl moiety, esters, the nitro group, and so forth. In this specification it is to be understood that the term "alkyl" refers both to unsubstituted and substituted alkyl groups.

Both secondary and tertiary alkyl groups undergo rearrangement with the latter being preferred. Except for benzyl and similar arylmethyl groups, primary alkyl groups rearrange with difficulty, often with isomerization of the alkyl group itself, thereby limiting their utility in this invention. Examples of suitable alkyl groups include propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, benzyl, and so forth. Tertiary butyl ethers are especially desirable reactants in the invention herein.

The aromatic portion of the alkyl phenyl ethers of this invention may be the unsubstituted phenyl group itself, but in the more usual case the aromatic ring contains one or more groups which are otherwise inert, subject to the provision that at least one ortho position remains unsubstituted. Examples of inert ring substituents include the halogens, and the nitro, ester, and alkyl groups. Alkyl substituents are especially important, and the ring substituted alkyl group may be the same or different from the alkyl portion of the ether. The alkyl group may occupy any of the ring positions, but 2-alkyl phenyl alkyl ethers are especially desirable reactants. The most desirable ring-substituted alkyl groups are those containing up to about 10 carbon atoms. Examples include methyl, ethyl, propyl, butyl, pentyl, hexyl, heptyl, octyl, nonyl, and decyl groups. Illustrative examples of the aromatic portion of the alkyl phenyl ethers of this invention include 2-methylphenyl, 3-methylphenyl, 4-methylphenyl, 2,4-dimethylphenyl, 2-ethylphenyl, 4-ethylphenyl, 2-n-propylphenyl, 3-n-propylphenyl, 2-i-propylphenyl, 4-i-propylphenyl, 2,4-i-propylphenyl, 2-i-propyl-4-methylphenyl, 2-t-butylphenyl, 4-t-butylphenyl, 2-t-butyl-4-methylphenyl, 2-methyl-4-t-butylphenyl, the isomeric pentylphenyls, hexylphenyls, heptylphenyls, and so on.

Of particular interest are those tertiary alkyl phenyl ethers where the aromatic ring bears an alkoxy or hydroxy moiety. As stated previously, the alkoxy moiety is a powerful ortho-directing group in alkylation, so that alkylation of, e.g., a 4-alkoxyphenol generally leads to a mixture representing alkylation ortho to the alkoxy moiety as well as alkylation ortho to the phenolic hydroxyl. Contrastingly, rearrangement of a t-alkyl phenyl ether occurs with great regioselectivity, leading to introduction of the tertiary alkyl group virtually exclusively ortho to the oxygen whence it originated. Although such regioselectivity may be unimportant where the aromatic ring bears a hydroxy moiety, our method remains important for such compounds because it assures introduction of but one tertiary alkyl group into the ring. This is equivalent to monoalkylation of a dihydric phenol, which generally is difficult because activation of the aromatic ring by two hydroxy groups normally leads to dialkylation.

Thus, the favored reactants in our method are tertiary alkyl 4-alkoxyphenyl ethers or tertiary alkyl 4-hydroxyphenyl ethers, which afford as products 2-t-alkyl-4-alkoxyphenols and 2-t-alkyl-4-hydroxyphenols, respectively. In those cases where the reactant is a 4-alkoxyphenyl ether it is desirable that the alkyl portion of the alkoxy moiety by a primary alkyl group so it will not undergo rearrangement competitively with the tertiary alkyl portion of the ether, although under carefully controlled conditions a secondary alkyl group may be present. With this limitation in mind the alkyl portion of the alkoxy moiety has the same general description given above for ring alkyl substituents.

Particularly important as products are 2-t-butyl-4-alkoxyphenols, where the alkyl portion of the alkoxy moiety is a primary alkyl group containing from 1 to about 10 carbon atoms, and 2-t-butyl-1,4-hydroquinone, popularly known as TBHQ. The ethers which are reactants in the claimed rearrangement to the aforementioned products are the t-butyl 4-alkoxyphenyl ethers and t-butyl 4-hydroxyphenyl ether, respectively. The phenolic precursors to these ethers are 4-alkoxyphenols and 1,4-hydroquinone, respectively.

The alkyl phenyl ethers of this invention are caused to undergo a thermally induced rearrangement in contact with an alumina. Although any alumina will suffice, those aluminas whose acidity has been enhanced often are advantageous. One such group of aluminas are halided aluminas, especially chlorided and fluorided alumina, and particularly fluorided alumina. Fluorided alumina, for example, which is the product wherein fluoride ions have been deposited in the alumina matrix, may be prepared by contacting alumina with a solution of ammonium fluoride, evaporating the water while mixing, and calcining the resultant product. Another mode of preparation, by way of illustration, is passage of gaseous hydrogen fluoride over solid alumina, wherein the contact time and the total amount of hydrogen fluoride to which the alumina is exposed will determine the final fluoride content of the product.

The efficacy of the halided alumina catalyst in inducing thermal rearrangement depends upon the halide content of the catalyst. Preparations containing from about 0.3 to about 5 wt. % halide are preferred, and those from about 0.3 to about 3 wt. % halide are especially preferred.

Where the rearrangement occurs with particular facility, an alumina whose acidity has been decreased may be advantageous. One such group of aluminas are those containing alkali metal cations, especially lithium, in the alumina matrix. Where lithiated alumina is used for alkyl phenyl ethers particularly prone to rearrangement, little isomerization of the ortho-alkylated product occurs subsequent to formation. Lithiated alumina containing from about 0.3 to about 5 wt. % lithium is preferred, with those from about 0.5 to about 3% being especially preferred.

Silica-alumina containing up to about 75% silica may also be used as a catalyst in this invention. Some silica-aluminas, being substantially more acidic than, for example, fluorided alumina, are somewhat less efficaceous than the latter in the selectivity of the rearrangement to ortho-alkylated product. A halided silica-alumina also may be used in the practice of this invention.

The amount of alumina used in the practice of this invention depends upon the nature of the alkyl group, that is, whether secondary or tertiary, and the rate of rearrangement desired. When the reaction is run in a batch mode the amount of alumina used may vary from about 0.1 to over 100% by weight relative to the ether to be rearranged.

The ether is contacted with an alumina under rearrangement conditions. The temperature at which rearrangement occurs may be from about 65° C. to about 200° C. depending upon the nature of the alkyl group. It has been found that a tertiary group undergoes rearrangement substantially more readily than does a secondary alky group. Where a tertiary alkyl group undergoes rearrangement a temperature from about 65° to about 150° C. generally suffices. Since pressure has no important effect on this reaction rearrangement generally is performed under autogeneous pressure.

Conversion of phenols to tertiary alkyl phenyl ethers may be performed by any method known in the art. An example of a preparative route is the reaction of a phenol with an alcohol in the presence of an acid catalyst, such as a strong inorganic acid or a cationic exchange resin bearing sulfonic acid groups. Another preparative route is the reaction of a phenol with an olefin in the presence of a Lewis acid, such as an inorganic oxide as alumina or a metal halide. It is to be understood that the conversion of a phenol to its tertiary alkyl phenyl ether is well known in the art and need not be described here in any great detail.

The following Example is illustrative of this invention and is not to be construed as limiting the invention thereto.

EXAMPLE

To a 300 cc stainless steel stirred autoclave may be added 124 g (1.0 mol) 4-methoxyphenol and 10 g of XN-1010, a cation exchange resin bearing sulfonic acid groups supplied by Rohm and Haas Co. The system may be charged with 56 g (1.0 mol) isobutylene and the mixture stirred 5 hours at 20° C. Resin may be removed by filtration and unreacted phenol may be removed by washing the filtrate with an aqueous solution of 10% sodium hydroxide. The organic material may be washed with water to remove caustic and dried with magnesium sulfate to afford t-butyl 4-methoxyphenyl ether in a yield of about 70%.

A solution of 50 g of t-butyl 4-methoxyphenyl ether in about 50 ml hexane mixed with 5 g alumina may be heated to reflux with stirring until disappearance of starting material is confirmed by gas liquid phase chromatography. The cooled mixture may be filtered to remove alumina, and solvent may be removed from the filtrate by evaporation to afford 4-methoxy-2-t-butylphenol. The latter may be further purified by fractional distillation.

What is claimed is:

1. A method of rearranging a t-alkyl 4-alkoxyphenyl ether or a t-alkyl-4-hydroxyphenyl ether to a 2-t-alkyl-4-alkoxyphenol or a 2-t-alkyl-4-hydroxyphenol, respectively, comprising heating said ether in contact with an alumina selected from the group consisting of alumina, aluminas containing an alkali metal cation in the matrix, lithiated alumina, and silica-alumina at a temperature from about 65° C. to about 150° C. and recovering the formed phenol.

2. The method of claim 1 where both ortho-positions of the aromatic ring in the ether are occupied by hydrogen.

3. The method of claim 1 where the phenyl portion of the ether bears an alkyl moiety at the position ortho to the t-alkyl ether moiety.

4. The method of claim 1 where the alumina is a halided alumina.

5. The method of claim 4 where the alumina is a fluorided alumina.

6. The method of claim 1 where the alumina is a lithiated alumina.

7. The method of claim 1 where the alumina is a silica-alumina containing up to about 75% silica.

8. The method of claim 1 where the ether is a tertiary butyl ether.

9. The method of claim 8 where the ether is t-butyl 4-methoxyphenyl ether or t-butyl 4-hydroxyphenyl ether and the phenol is 2-t-butyl-4-methoxyphenol or 2-t-butyl-4-hydroxyphenol, respectively.

10. A method of ortho-alkylating a 4-alkoxyphenol or 4-hydroxyphenol comprising converting the phenol to a t-alkyl phenyl ether, heating the ether in contact with an alumina selected from the group consisting of alumina, aluminas containing an alkali metal cation in the matrix, lithiated alumina, and silica-alumina at a temperature from about 65° C. to about 150° C., and recovering the formed 2-t-alkyl-4-alkoxyphenol or 2-t-alkyl-4-hydroxyphenol, respectively.

11. The method of claim 10 where the phenol bears an alkyl moiety ortho to the phenolic hydroxyl moiety.

12. The method of claim 10 where the alumina is a halided alumina.

13. The method of claim 12 where the alumina is a fluorided alumina.

14. The method of claim 10 where the alumina is lithiated alumina.

15. The method of claim 10 where the alumina is a silica-alumina containing up to about 75% silica.

16. The method of claim 10 where the ether is a tertiary butyl ether.

17. The method of claim 10 where the phenol is 1,4-hydroquinone or 4-methoxyphenol and the ether is the tertiary butyl ether.

* * * * *